(12) United States Patent
Wang et al.

(10) Patent No.: US 7,829,747 B2
(45) Date of Patent: Nov. 9, 2010

(54) PROCESS FOR DEHYDROFLUORINATION OF 3-CHLORO-1,1,1,3-TETRAFLUOROPROPANE TO 1-CHLORO-3,3,3-TRIFLUOROPROPENE

(75) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/419,002

(22) Filed: Apr. 6, 2009

(65) Prior Publication Data
US 2009/0270661 A1    Oct. 29, 2009

Related U.S. Application Data

(60) Provisional application No. 61/047,613, filed on Apr. 24, 2008.

(51) Int. Cl.
   *C07C 17/00*    (2006.01)

(52) U.S. Cl. .................................................. 570/156
(58) Field of Classification Search ................. 570/156
   See application file for complete search history.

(56) References Cited

U.S. PATENT DOCUMENTS

| 5,710,352 A | 1/1998 | Tung |
| 6,844,475 B1 | 1/2005 | Tung et al. |
| 2005/0090698 A1* | 4/2005 | Merkel et al. ............... 570/155 |

* cited by examiner

*Primary Examiner*—Jafar Parsa
(74) *Attorney, Agent, or Firm*—Bruce O. Bradford

(57) ABSTRACT

A process for making 1-chloro-3,3,3-trifluoropropene. The process has the following step: dehydrofluorinating 3-chloro-1,1,1,3-tetrafluoropropane under conditions sufficient to effect dehydrofluorination in the presence of a catalyst. Preferred catalysts are selected from the group consisting of (i) one or more halogenated trivalent or higher valent metal oxides, (ii) one or more trivalent or higher valent metal halides, and (iii) one or more natural or synthetic graphite materials.

20 Claims, No Drawings

PROCESS FOR DEHYDROFLUORINATION OF 3-CHLORO-1,1,1,3-TETRAFLUOROPROPANE TO 1-CHLORO-3,3,3-TRIFLUOROPROPENE

CROSS-REFERENCE TO A RELATED APPLICATION

The present application claims priority from U.S. Provisional Application No. 61/047,613, filed Apr. 24, 2008, which is incorporated herein in its entirety.

BACKGROUND OF THE INVENTION

1. Field of the Invention

The present invention relates to a process for dehydrohalogenation of a halogen-containing compound. The present invention further relates to a process for dehydrofluorination of 3-chloro-1,1,1,3-tetrafluoropropane to 1-chloro-3,3,3-trifluoropropene.

2. Description of the Related Art 1-chloro-3,3,3-trifluoropropene (HCFC-1233zd, which has two isomers, trans-CHCl=CHCF$_3$ and cis-CHCl=CHCF$_3$) can be used as a refrigerant, a blowing agent, solvent, cleaning agent, and as a monomer in the synthesis of macromolecular compounds, including polymeric materials and other fluorinated compounds.

The prior art discloses various processes for making HCFC-1233zd. U.S. Pat. No. 5,710,352 discloses a vapor phase process for making 1,1,3,3,3-pentafluoropropane and HCFC-1233zd by reacting 1,1,1,3,3-pentachloropropane with hydrogen fluoride in the presence of a fluorination catalyst. U.S. Pat. No. 6,844,475 discloses a low-temperature liquid phase process for making HCFC-1233zd by reacting 1,1,1,3,3-pentachloropropane with hydrogen fluoride in the presence of a Lewis acid catalyst or mixture of Lewis acid catalysts.

It would be desirable to have an efficient process for making HCFC-1233zd at high selectivity.

SUMMARY OF THE INVENTION

According to the present invention, there is provided a process for making 1-chloro-3,3,3-trifluoropropene (HCFC-1233zd). The process has the following step: dehydrofluorinating 3-chloro-1,1,1,3-tetrafluoropropane (244fa) under conditions sufficient to effect dehydrofluorination in the presence of a catalyst. Preferred catalysts are selected from the group consisting of (i) one or more halogenated trivalent or higher valent metal oxides, (ii) one or more trivalent or higher valent metal halides, and (iii) one or more natural or synthetic graphites.

DETAILED DESCRIPTION OF THE INVENTION

HCFC-1233zd can be prepared from 244fa in the presence of a catalyst. With a selection of a preferred catalyst, the reaction can be carried out at high selectivity. The reaction is selective relative to a competing dehydrochlorination reaction to HFC-1234ze, which has two isomers, trans-CHF=CHCF$_3$ and cis-CHF=CHCF$_3$.

The reaction can be carried out at high selectivity in the presence of any of three classes of catalysts. The catalysts are (i) halogenated trivalent and higher valent metal oxides, (ii) trivalent and higher valent metal halides, and (iii) natural and synthetic graphites. Combinations of catalysts within the classes and among the classes are also possible.

For the catalysts of halogenated trivalent and higher valent metal oxides and combinations thereof, suitable metal ion(s) include, but are not limited to, the following: $Al^{3+}$, $Ga^{3+}$, $In^{3+}$, $Sc^{3+}$, $Y^{3+}$, $La^{3+}$, $Cr^{3+}$, $Fe^{3+}$, $Co^{3+}$, $Ti^{4}$, $Zr^{4+}$, $Ce^{4+}$, $Sn^{4+}$, $Mn^{4+}$, $Nb^{5+}$, and $W^{6+}$. Useful agents for halogenating metal oxides to form the catalysts include, but are not limited to, the following: HF, $F_2$, HCl, $Cl_2$, HBr, $Br_2$, HI, and $I_2$. The catalyst can be unsupported or supported on a substrate. Useful catalyst supports include, but are not limited to, the following: activated carbon, graphite, silica, alumina, fluorinated alumina, and fluorinated graphite.

For the catalysts of trivalent and higher valent metal halides and combinations thereof, metal ions included in the catalyst can be, but are not limited to, the following: $Al^{3+}$, $Ga^{3+}$, $In^{3+}$, $Sc^{3+}$, $Y^{3+}$, $La^{3+}$, $Cr^{3+}$, $Fe^{3+}$, $Co^{3+}$, $Ti^{4}$, $Zr^{4+}$, $Ce^{4+}$, $Sn^{4+}$, $Mn^{4+}$, $Nb^{5+}$, and $W^{6+}$. The halogen (X) included in the catalyst can be F, Cl, Br, or I. The catalyst is either unsupported or supported on a substrate. Useful supports include, but are not limited to, the following: activated carbon, graphite, silica, alumina, fluorinated alumina, and fluorinated graphite.

Useful graphite catalysts include both natural and synthetic graphites. Useful natural graphites include, but are not limited to, crystalline flake graphite, amorphous graphite, and lump graphite.

The catalyst may be regenerated as needed to maintain a desired level of activity. Regeneration may be accomplished by any in-situ treatment known in the art. One treatment is to pass an oxygen flow or oxygen diluted with nitrogen over the catalyst at temperatures of from about 200° C. to about 600° C. and preferably from about 350° C. to about 450° C. for from about 0.5 hour to about 3 days. The passing of oxygen-containing gas is followed by treatment with HF treatment at temperatures of from about 200° C. to about 600° C. and preferably from about 300° C. to about 400° C. The foregoing treatment is particularly useful for halogenated trivalent or higher valent metal oxide catalysts and trivalent or higher valent metal halide catalysts.

The dehydrofluorination reaction is preferably carried out in a gas phase in the presence of a catalyst. In less preferred embodiments, it is possible to carry out such reaction in a liquid phase.

Desirable levels of 244fa conversion and 1233zd selectivity can be impacted by operating parameters, including conditions such as reaction temperature, pressure, and residence time. The reaction will be carried out at conditions sufficient to effect dehydrofluorination. Selectivity for the dehydrofluorination reaction to HCFC-1233zd with the preferred catalysts is about 50% or more, more preferably about 70 or more, and most preferably about 95% or more. Conversion of 244fa is preferably about 10% or more, more preferably about 50% or more, and most preferably about 90% or more.

Dehydrofluorination is carried out at a temperature sufficient to achieve desired conversion levels. Reaction temperature refers to the average temperature in the catalyst bed. The reaction temperature preferably ranges from about 100° C. to about 600° C., more preferably from about 250° C. to about 450° C., still more preferably from about 300° C. to about 400° C., and most preferably from about 300° C. to about 350° C.

Dehydrofluorination can be carried out over a wide range of pressures, as pressure is not a particularly critical reaction condition. Reactor pressure can be superatmospheric, atmospheric, or under vacuum. In preferred embodiments however, the reaction is carried out under pressure conditions ranging from about 1 to about 20 atm and more preferably from about 2 to about 6 atm.

Dehydrofluorination can be carried out over a wide range of residence times, as residence time is not a particularly critical reaction condition. In preferred embodiments however, residence time may range from about 0.5 second to about 600 seconds and more preferably from about 10 to about 60 seconds.

Dehydrofluorination typically yields a reaction product having the 1-chloro-3,3,3-trifluoropropene and one or more compounds other than 1-chloro-3,3,3-trifluoropropene. The reaction product typically takes the form of a mixture of the following: unreacted starting materials, e.g., 244fa; target products, e.g., HCFC-1233zd; and by-products, e.g., HF, HCl, HFC-1234ze, and 1,1,1,3,3-pentafluoropropane (245fa). HCFC-1233zd may be recovered from the reaction product as either or both of the cis and trans isomers thereof.

Recovery of compounds from the reaction product may be effected by any means known in the art, such as by extraction and preferably by distillation. For example, the distillation may be conducted in a standard distillation column at a pressure less than about 300 psig, preferably less than about 150 psig, and most preferably less than 100 psig. The pressure of distillation column inherently determines the distillation operating temperature. HCl may be recovered by operating the distillation column at from about −40° C. to about 25° C., preferably from about −40° C. to about −20° C. HCFC-1233zd and HFC-1234ze may be recovered by operating the distillation column at from about −10° C. to about 60° C. Single or multiple distillation columns may be used. If, desired, the trans-CHCl=CHCF$_3$ and cis-CHCl=CHCF$_3$ components of HCFC-1233zd may be separated from each other by means known in the art, such as extraction and distillation.

In a preferred embodiment, the HCl is removed from the reaction products. More preferably, the HCl is removed prior to the recovery of HCFC-1233zd from the reaction product mixture. Optionally but preferably, HF may be recovered. Recovery of HF can be conducted by passing remaining product mixture through a sulfuric acid extractor to remove HF, subsequently desorbing the extracted HF from the sulfuric acid, and then distilling the desorbed hydrogen fluoride.

EXAMPLES

Example 1

244fa Dehydrohalogenation Over a Fluorinated Metal Oxide Catalyst

In Example 1, fluorinated $Cr_2O_3$ was used as a dehydrofluorination catalyst. 20 cc of catalyst was charged into a ¾-inch Monel reactor. 244fa feed was passed through the catalyst at a rate of 12 grams/hour at a temperature of 350° C.

As shown in Table 1, the fluorinated $Cr_2O_3$ catalyst provided a 1233zd selectivity of about 75% and a 1234ze selectivity of about 20%. Thus, the $Cr_2O_3$ catalyst is much more active (selective) for 244fa dehydrofluorination than for dehydrochlorination. All 244fa was converted during the reaction.

TABLE 1

(244fa dehydrohalogenation over a fluorinated metal oxide catalyst at 350° C.)

| Catalyst | Conversion (%) 244fa | Selectivity (%) | | | |
|---|---|---|---|---|---|
| | | t/c-1234ze | 245fa | t/c-1233zd | others |
| Fluorinated $Cr_2O_3$ | 100.0 | 20.7 | 0.0 | 74.6 | 4.7 |

Example 2

244fa Dehydrohalogenation Over Supported and Unsupported Metal Halide Catalysts In Example 2, two trivalent metal halides and one tetravalent metal fluoride were used as dehydrofluorination catalysts. 20 cc of each catalyst was charged into a ¾-inch Monel reactor. 244fa feed was passed through each catalyst at a rate of 12 grams/hour at a temperature of 350° C. As shown in Table 2, for all the three catalysts, 1233zd was generated as the major product. In addition, almost all 244fa was converted over $FeCl_3$ and $AlF_3$ catalysts, while about 68% of 244fa was converted over a $CeF_4$ catalyst.

TABLE 2

(244fa dehydrohalogenation over supported and unsupported metal halide catalysts at 350° C.)

| LiCl loading (wt %) | Conversion (%) 244fa | Selectivity (%) | | | |
|---|---|---|---|---|---|
| | | t/c-1234ze | 245fa | t/c-1233zd | others |
| 10 wt % $FeCl_3$/Carbon | 99.4 | 7.1 | 15.1 | 77.3 | 0.4 |
| $AlF_3$ | 100.0 | 21.8 | 0.0 | 77.3 | 0.9 |
| $CeF_4$ | 68.4 | 5.1 | 19.2 | 66.4 | 9.3 |

Example 3

244fa Dehydrohalogenation Over a Graphite Catalyst

In Example 3, Alfa Aesar Graphite Flake was used as dehydrofluorination catalyst. 20 cc of catalyst was charged into a ¾-inch Monel reactor. 244fa feed was passed through catalyst at a rate of 12 grams/hour at a temperature of 350° C. As shown in Table 3, the graphite catalyst provided a 1233zd selectivity of about 95% and a 1234ze selectivity of below 5%. Thus, the graphite catalyst is much more active for 244fa dehydrofluorination than for dehydrochlorination. About 27% of 244fa was converted during reaction.

TABLE 3

(244fa dehydrohalogenation in the presence of a graphite catalyst at 350° C.)

| Catalyst | Conversion, % 244fa | Selectivity (%) | | | |
|---|---|---|---|---|---|
| | | t/c-1234ze | 245fa | t/c-1233zd | others |
| Alfa Aesar Graphite Flakes | 27.3 | 3.2 | 0.0 | 95.5 | 1.3 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for making 1-chloro-3,3,3-trifluoropropene, comprising: dehydrofluorinating 3-chloro-1,1,1,3-tetrafluoropropane under conditions sufficient to effect dehydrofluorination in the presence of a catalyst.

2. The process of claim 1, wherein the catalyst is selected from the group consisting of (i) one or more halogenated trivalent or higher valent metal oxides, (ii) one or more trivalent or higher valent metal halides, (iii) one or more natural or synthetic graphites, and (iv) combinations thereof.

3. The process of claim 1, wherein the dehydrofluorinating is carried out in the vapor phase.

4. The process of claim 2, wherein the dehydrofluorinating is carried out in the vapor phase.

5. The process of claim 2, wherein the catalyst is the one or more halogenated trivalent or higher valent metal oxides.

6. The process of claim 5, wherein the metal ion of the catalyst is selected from the group consisting of $Al^{3+}$, $Ga^{3+}$, $In^{3+}$, $Sc^{3+}$, $Y^{3+}$, $La^{3+}$, $Cr^{3+}$, $Fe^{3+}$, $Co^{3+}$, $Ti^{4+}$, $Zr^{4+}$, $Ce^{4+}$, $Sn^{4+}$, $Mn^{4+}$, $Nb^{5+}$, $W^{6+}$, and combinations thereof.

7. The process of claim 2, wherein the catalyst is the one or more trivalent or higher valent metal halides.

8. The process of claim 7, wherein the metal ion(s) is selected from the group consisting of $Al^{3+}$, $Ga^{3+}$, $In^{3+}$, $Sc^{3+}$, $Y^{3+}$, $La^{3+}$, $Cr^{3+}$, $Fe^{3+}$, $Co^{3+}$, $Ti^{4+}$, $Zr^{4+}$, $Ce^{4+}$, $Sn^{4+}$, $Mn^{4+}$, $Nb^{5+}$, and $W^{6+}$, and combinations thereof.

9. The process of claim 2, wherein the catalyst is the one or more natural or synthetic graphites.

10. The process of claim 1, wherein the dehydrofluorinating is carried out is carried out at a temperature from about 100° C. to about 600° C.

11. The process of claim 2, wherein the dehydrofluorinating is carried out is carried out at a temperature from about 100° C. to about 600° C.

12. The process of claim 1, wherein the dehydrofluorinating is carried out is carried out at a pressure from about 1 atm to about 20 atm.

13. The process of claim 2, wherein the dehydrofluorinating is carried out is carried out at a pressure from about 1 atm to about 20 atm.

14. The process of claim 1, wherein the dehydrofluorinating is carried out is carried out for a residence time from about 0.5 second to about 600 seconds.

15. The process of claim 2, wherein the dehydrofluorinating is carried out is carried out for a residence time from about 0.5 second to about 600 seconds.

16. The process of claim 1, wherein the catalyst is supported.

17. The process of claim 1, wherein the catalyst is unsupported.

18. The process of claim 1, wherein the dehydrofluorination yields a reaction product having the 1-chloro-3,3,3-trifluoropropene and one or more compounds other than 1-chloro-3,3,3-trifluoropropene.

19. The process of claim 18, wherein the dehydrofluorination is followed by a separation of 1-chloro-3,3,3-trifluoropropene from the reaction product.

20. The process of claim 19, wherein the dehydrofluorination is followed by a separation of either the trans isomer or the cis isomer of 1-chloro-3,3,3-trifluoropropene from the reaction product.

* * * * *